(12) United States Patent
Arndt

(10) Patent No.: US 7,036,376 B2
(45) Date of Patent: May 2, 2006

(54) DEVICE FOR EVALUATING SIGNALS

(75) Inventor: Volker Arndt, Erbach (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/469,463

(22) PCT Filed: Feb. 12, 2002

(86) PCT No.: PCT/DE02/00509

§ 371 (c)(1),
(2), (4) Date: Feb. 5, 2004

(87) PCT Pub. No.: WO02/071091

PCT Pub. Date: Sep. 12, 2002

(65) Prior Publication Data

US 2004/0107774 A1 Jun. 10, 2004

(30) Foreign Application Priority Data

Mar. 2, 2001 (DE) ................................. 101 10 045

(51) Int. Cl.
*G01N 29/20* (2006.01)
*B23K 11/25* (2006.01)
(52) U.S. Cl. ........................ 73/599; 73/602; 73/611; 219/109
(58) Field of Classification Search ............ 73/599, 73/602, 611, 600, 1.82, 1.86, 614; 219/506, 219/109
See application file for complete search history.

(56) References Cited

U.S. PATENT DOCUMENTS

| 3,958,451 | A |   | 5/1976  | Richardson             |
|-----------|---|---|---------|------------------------|
| 4,099,045 | A | * | 7/1978  | Okuda et al. ... 219/109 |
| 4,137,776 | A |   | 2/1979  | Rudis                  |
| 4,147,065 | A | * | 4/1979  | Lather et al. ... 73/611 |
| 4,213,183 | A |   | 7/1980  | Barron                 |
| 4,480,475 | A |   | 11/1984 | Tsao                   |
| 5,280,723 | A | * | 1/1994  | Aharoni et al. ... 73/602 |
| 5,439,157 | A |   | 8/1995  | Geier                  |
| 5,641,906 | A |   | 6/1997  | Moore                  |
| 5,920,014 | A | * | 7/1999  | Waschkies ... 73/597    |
| 6,510,389 | B1| * | 1/2003  | Winkler et al. ... 702/6 |

OTHER PUBLICATIONS

Patent Abstracts of Japan vol. 010, No. 030 (P-426), Feb. 5, 1986 & JP 60 181651 A, Sep. 17, 1985.

* cited by examiner

*Primary Examiner*—John E. Chapman
(74) *Attorney, Agent, or Firm*—Michael J. Striker

(57) ABSTRACT

A welding system includes a device for evaluating an ultrasonic signal during a welding process. The device has a meassured value evaluation unit that, in normal operation, evaluates at least one measurement signal that is derived from an ultrasonic signal and is located inside a measurement window. A mechanism for establishing the measurement window is provided, which establishes the measurement window according to a measurement signal that is received in a calibration operation.

13 Claims, 3 Drawing Sheets

DEVICE FOR EVALUATING SIGNALS

BACKGROUND INFORMATION

A method for assessing resistance-welded joints is made known in German Patent Application DE-A 43 25 878. In order to assess welds during the welding process itself, the ultrasonic permeability, or attenuation, of the welded joint is determined by acting upon said welded joint with shear waves. To accomplish this, the mean ultrasonic energy is determined from the output signal from the ultrasound receiver during each current half-cycle of the welding current within a time window that is delayed relative to the constant ultrasonic transmitted signal by a defined delay time. The mean ultrasonic energy is used as a measure of the quality of the welded joint. How the time window is selected and the time interval by which it should be delayed relative to the ultrasonic transmitted signal are left open, however.

The object of the present invention is to provide a device that allows the measurement window to be automatically adapted to different measurement situations.

SUMMARY OF THE INVENTION

The device, according to the present invention, for evaluating signals has a measured value evaluation unit that, in normal operation, further processes at least one measurement signal that is derived from an ultrasonic signal and is located inside a measurement window. According to the present invention, means for establishing the measurement window are provided that establish the measurement window according to a measurement signal that is received in a calibration operation. By taking the measurement signal into account immediately when selecting the measurement window, situations that are different in terms of environmental conditions can be taken into account automatically. In addition, the measurement window need not be manually adjusted anew each time. The measurement window is adjusted automatically before the beginning of the particular process, which is controlled by the measured value detection unit. As a result, less-qualified workers can also work with the corresponding measurement and controlling devices. In addition, the device can be used to indicate possible sources of error at an early point in time. When used for a resistance-welding system in particular, statements can be made at an early point in time about possible electrode wear. Additionally, welding tongs can be inspected during a pause in production.

In an advantageous further development, detection of elapsed time is provided that establishes the measurement window according to the elapsed time of the measurement signal. By taking into account the elapsed time based on a transmitted signal that effects the measurement signal, the measurement window can be matched to the particular process, since the process may influence the elapsed time. The accuracy of the evaluation method is increased as a result.

An advantageous further development provides a zero transition point determination of the measurement signal, with which the period interval of the measurement signal is determined, and that can also be used to establish the measurement window. The measurement window preferably begins and ends at a zero transition point. In addition, statements can also be made about whether the frequencies of the transmitted signal and the measurement signal that are capable of being determined in this manner approximately match. The measurement window is established such that those measured values are taken into account whose frequency and period interval approximately match those of the transmitted signal. As a result, only meaningful measured values are evaluated.

In an advantageous further development, an extreme value determination of the measured signal is provided, the output signal of which is used to establish the measurement window. The measurement window can now be selected such that the extreme values (maximum, minimum) of the measured values are located within the measurement window and are used for further processing.

In an advantageous embodiment, the measured value is an ultrasonic signal that is evaluated in order to assess the quality and/or control of a welded joint, in particular a resistance-welded joint.

Additional advantageous further developments result from further dependent claims and from the description.

BREIF DESCRIPTION OF THE DRAWINGS

An exemplary embodiment of the invention is shown in the drawing and will be described in greater detail hereinbelow.

DETAILED DESCRIPTION OF THE PREFERRED EMBODIMENTS

Figure 1:
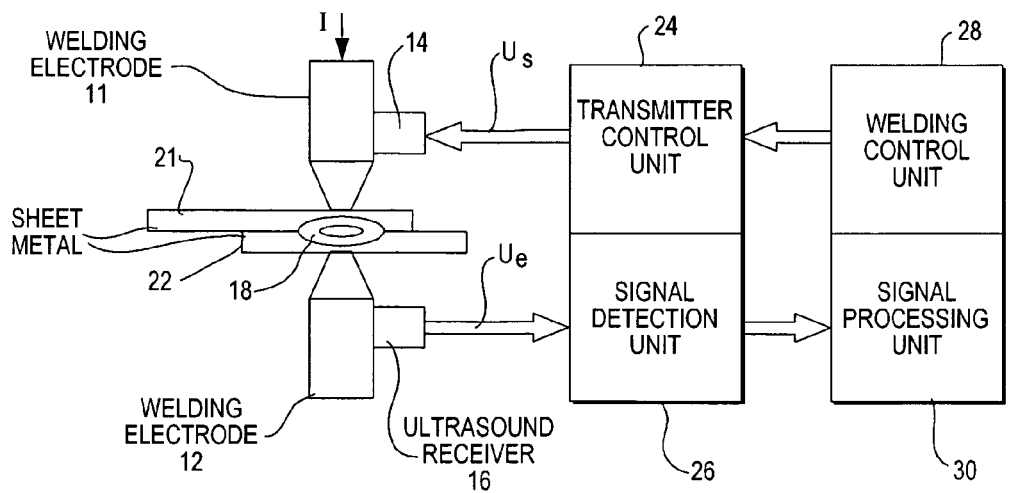
FIGS. 1 and 2 show a block diagram of the device according to the present invention.

A first welding electrode 11 is acted upon with a current i. An ultrasonic transmitter 14 is situated on the first welding electrode 11. An ultrasound receiver 16 is situated on the outer wall of a second welding electrode 12. A first piece of sheet metal 21 and a second piece of sheet metal 22—that are joined by a weld point 18—are located between the two electrodes 11 and 12. The ultrasonic transmitter 14 is acted upon by a transmitted signal $U_S$ that is made available by a transmitter control unit 24 according to a trigger signal Trig from a welding control unit 28. The transmitted signal $U_S$ is guided through the first electrode 11, the first and second pieces of sheet metal 21, 22, the welding spot 18 and through the second electrode 12 to the ultrasound receiver 16. The ultrasound receiver 16 sends a measurement signal $U_e$ to a signal detection unit 26. The signal detection unit 26 forwards the detected measurement signal further to a signal processing unit 30.

Figure 2:
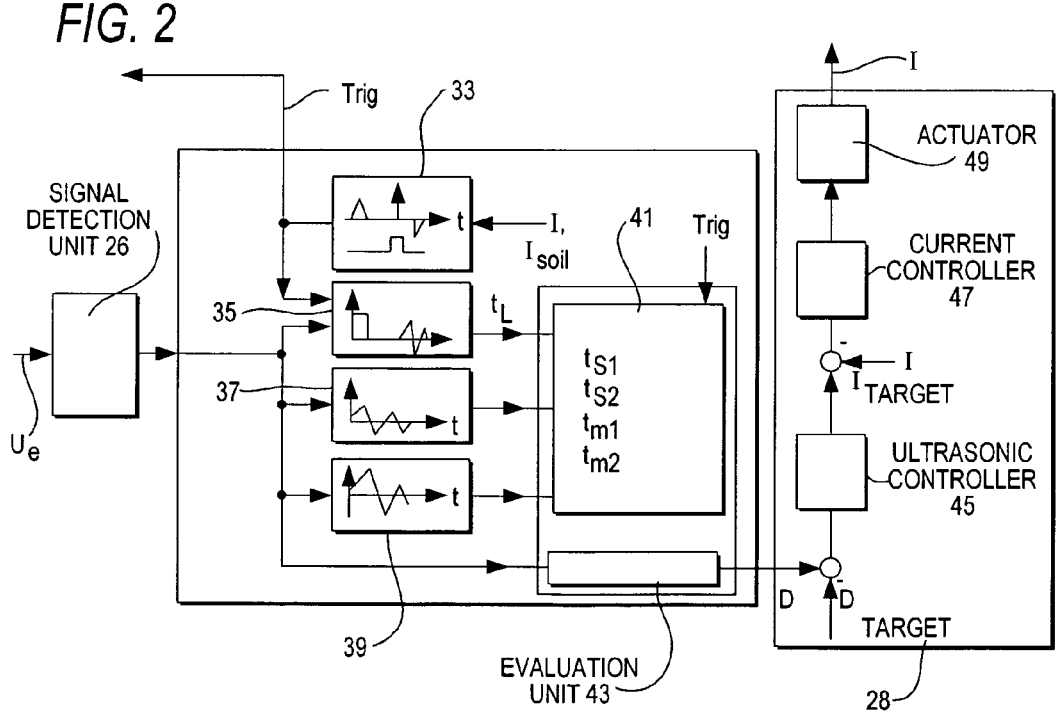

The design of the welding control unit 28 and the signal processing unit 30 is shown in greater detail in FIG. 2. The measurement signal $U_e$ detected by the signal detection unit 26 reaches the following four functional units. An elapsed-time determination unit 35 determines—depending on the trigger signal Trig and the measurement signal KE—the elapsed time $t_L$ for a measurement window determination unit 41. Additionally, a zero transition point determination unit 37 is provided, as well as an extreme value determination unit 39, each of which sends their output signals to the measurement window determination unit 41. This measurement window determination unit establishes the measurement window and its parameters $t_{m1}$, $t_{m2}$, $t_{S1}$, $t_{S2}$. Depending on the measurement window, a measured value evaluation unit 43 evaluates the output signal from the signal detection unit 26 and, from this, determines the actual value of the attenuation, or permeability D. The attenuation or permeability D is an input variable for the welding control unit 28.

The difference between the determined attenuation or permeability D and the target attenuation or permeability $D_{target}$ is calculated at a first summing point and forwarded to an ultrasonic controller 45. Based on this, the ultrasonic controller 45 determines a current target value $I_{target}$. The difference between the current target value $I_{target}$ and the current actual value I is calculated at a second summing point. A current controller 47 receives the difference as an input variable and uses it to generate a triggering signal for an actuator 49. The actuator 49 effects the desired current flow I through the electrodes 11, 12 to generate a weld point 18 that joins the pieces of sheet metal 21, 22. Additionally, a trigger generator 33 is provided in the signal processing unit 30, that evaluates the current flow I in order to generate a trigger signal Trig. The trigger generator 33 could also be integrated in the welding control unit 28.

Figure 3A:
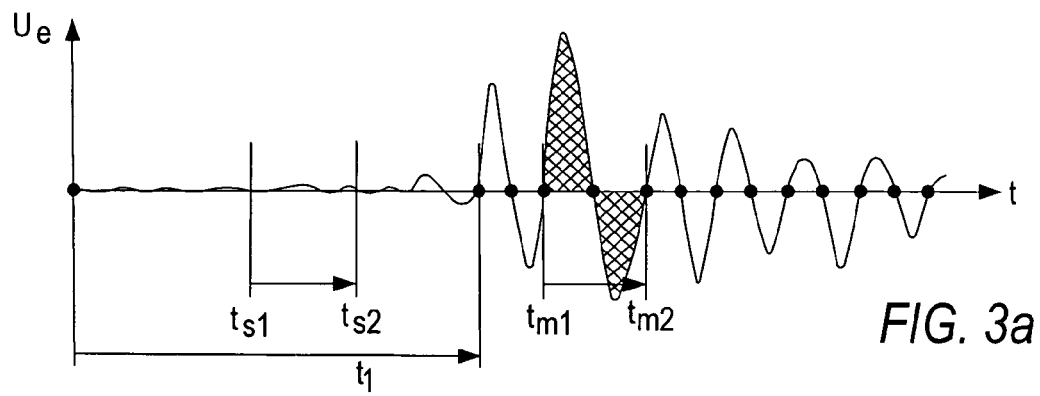
FIGS. 3a, 3b, 4a through 4c show characteristic time-dependent signal traces.
Figure 3B:
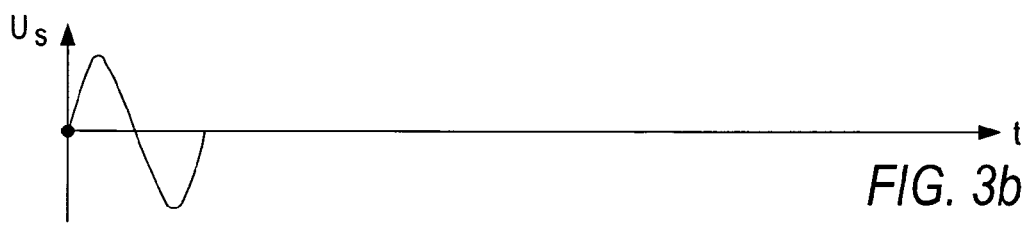

FIG. 3a shows the course of the measurement signal $U_e$ over time. At the instant t=0, the ultrasonic transmitter 14 emits a transmitted signal $U_s$ that contains a sinusoidal oscillation (FIG. 3b). After the elapsed time $t_L$, the ultrasound receiver 16 detects the measurement signal $U_e$, whose amplitude of sinusoidal oscillation first increases but then decreases in terms of amount, and dies out. The interference window is placed within the elapsed time $t_L$, the interference window being established by parameters $t_{S1}$ and $t_{S2}$. The same applies for the measurement window with parameters $t_{m1}$ and $t_{m2}$.

Figure 4A:
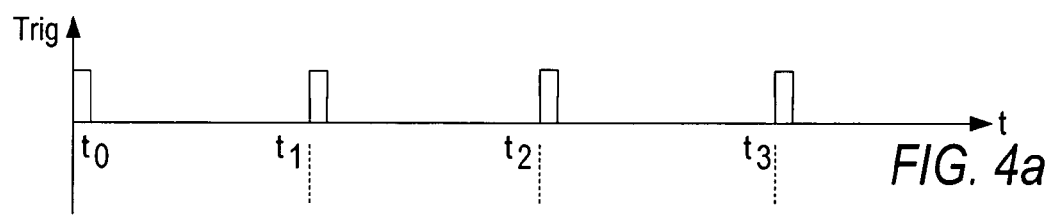
Figure 4B:
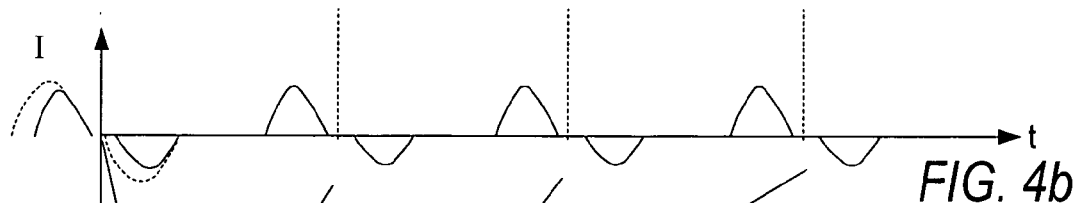
Figure 4C:
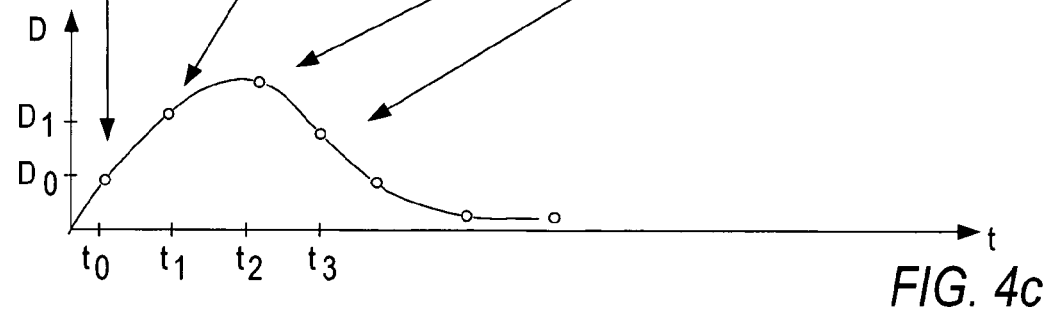

In normal operation, the resistance welding system is acted upon with a discontinuous current I having sinusoidal half-waves (FIG. 4b). The current intensity I is capable of being influenced by changing the variable, as shown with the dashed line. Depending on the current trace I according to FIG. 4b, the course of the trigger signal Trig results. The trigger signal Trig is selected such that a measurement is started by the emission of the transmitted signal $U_S$ specifically when no current I flows. The attenuation or permeability D as a function of time is shown in FIG. 4c. The attenuation or permeability curve of a good weld has the shape shown in the illustration. Only those measured values contribute to the determination of attenuation or permeability that are located within the measurement window $t_{m1}$, $t_{m2}$. The trigger signal Trig activates emission of the transmitted signal $U_S$.

Figure 5:
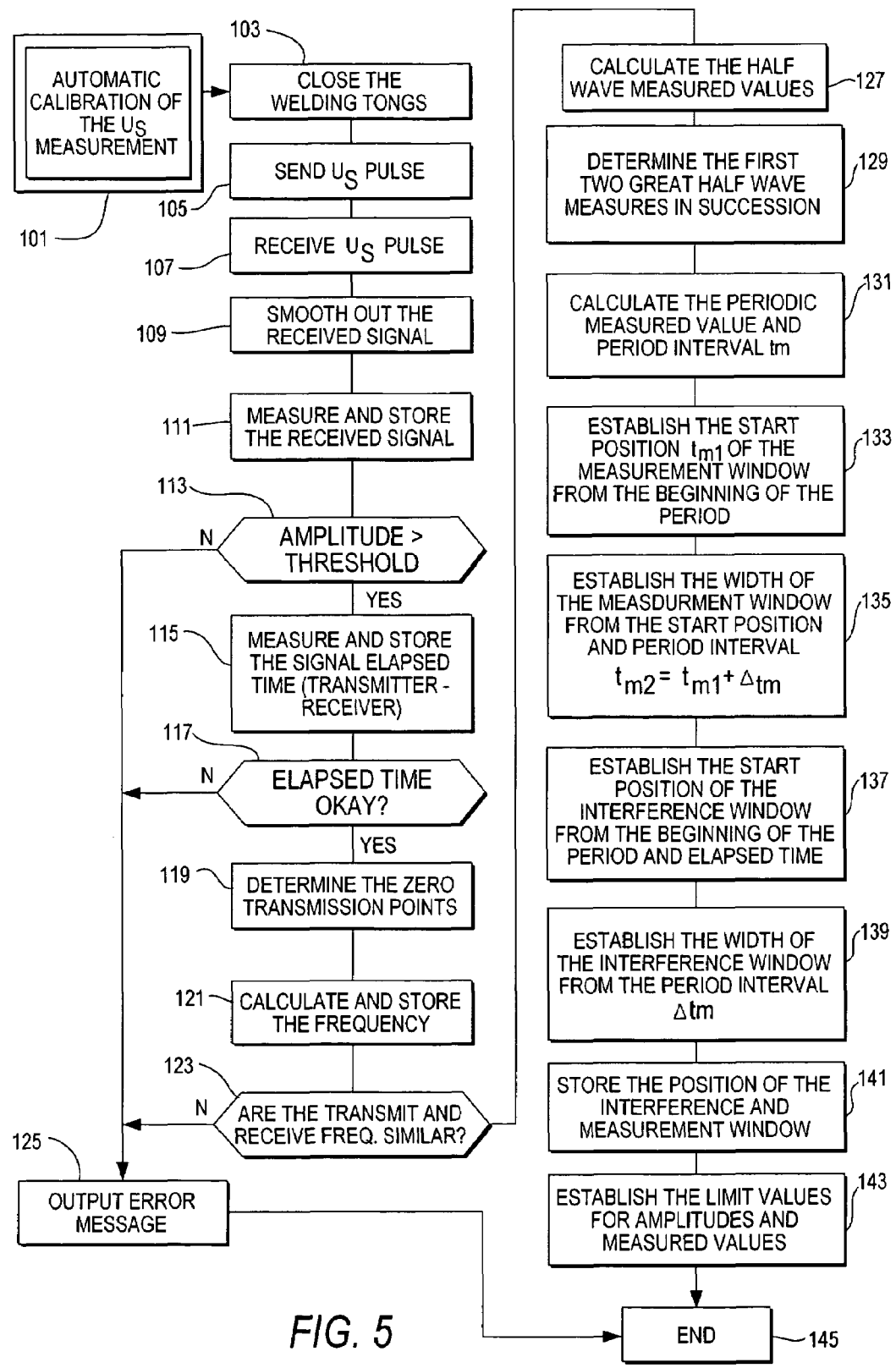
FIG. 5 shows a flow chart for operating the device.

The establishment of a measurement and/or interference window $t_{m1}$, $t_{m2}$, $t_{S1}$, $t_{S2}$ is described with reference to the flow chart in FIG. 5. The automatic calibration of the ultrasonic measurement device is activated by the start of the welding process (Step 101). Thereupon, the welding control unit closes the welding tongs formed by the two electrodes 11, 12 (Step 103). The transmitter control unit 24 then triggers the ultrasonic transmitter 14 to output a transmitted signal $U_S$ that has the shape shown in FIG. 3b (Step 105). The ultrasonic transmitter 14 preferably emits shear waves that propagate in the walls of the electrodes 11, 12 and that the ultrasound receiver 16 receives and forwards in the form of the measured signal $U_e$ to the signal detection unit 26 (Step 107). The signal detection unit 26 smooths the measurement signal $U_e$ using appropriate filters (Step 109). The course of the amplitude of the measurement signal $U_e$ over time is measured and stored, so that the signal trace of the measurement signal $U_e$ shown in FIG. 3a is available to devices 35, 37, 39, 43 (Step 111). In query 113, it is determined if the amplitude of the measurement signal $U_e$ exceeds a threshold in terms of amount within a specifiable time period (Query 113). If this is not the case, an error is determined to have occurred, because a measurement signal $U_e$ did not arrive at the ultrasound receiver 16. An appropriate error message is output (Step 125).

Otherwise, the elapsed time $t_L$ between the transmitted signal $U_S$ and the measurement signal $U_e$ is determined by the elapsed time determination unit (Step 115). The trigger point Trig and, therefore, the start of the transmitted signal $U_S$, is known. The trigger signal starts a counter that serves to detect time. The counter is not stopped until the amplitude of the measurement signal $U_e$ exceeds a certain threshold value in terms of amount. This threshold value is selected such that interfering signals are not detected. The elapsed time $t_L$ determined in this manner is shown in FIG. 3a. If the ultrasonic transmitter 14 and the ultrasound receiver 16 are located 110 mm apart, for example, the (theoretical) elapsed time $t_L$ is of the magnitude of 50 µs. Depending on this variable that is determined by calculation, a limit value can be established with which the elapsed time $t_L$ determined in Step 115 is compared (Step 117). The measurement signal $U_e$ should be within the limit value or exceed the specifiable amplitude threshold value, otherwise an error exists (Step 125).

Subsequently, the zero transition point determination unit 37 determines the zero transition points of the amplitude of the measurement signal $U_e$ (Step 119). The instants at which the amplitude of the measurement signal $U_e$ assumes the value "zero" are therefore known. Based on the instants at which the zero transition points occur, the associated period intervals and frequencies can be determined and stored (Step 121). With a sinusoidal measurement signal $U_e$, the three first measured values form the first period interval, the reciprocal value of which corresponds to the frequency of the measurement signal $U_e$. The second period interval results from the third to fifth zero transition point with associated frequency. In this manner, it is possible to associate frequencies with the particular positive and negative half-waves. The frequency of the transmitted signal $U_S$ is known as well. The frequencies determined in Step 121 are compared with the transmit frequency of the transmitted signal $U_S$ (Query 123). If the transmit frequency and measurement signal frequency deviate from each other only slightly, a meaningful measurement signal $U_e$ was obtained. Otherwise an error message is output in Step 125.

In Step 127, "half-wave measured values" are then calculated from the course of the measurement signal $U_e$ over time that was determined in Step 115. The root-mean-square value, the arithmetic mean or another measure of the energy content of a half-wave of the measurement signal $U_e$ is determined as the half-wave measured value. The appropriate half-wave measured value is therefore available for every half-wave (positive or negative) of the measurement signal $U_e$.

In subsequent Step 129, the two first greatest half-wave measured values in succession are determined by the extreme value determination unit 39 by the fact, for instance, that the root-mean-square value of the measurement signal $U_e$ exceeds a specifiable threshold. In the signal trace according to FIG. 3a, they are the two half-waves that each enclose a shaded area. The area enclosed by the particular half-wave is a measure of the corresponding half-wave measured value and/or the root-mean-square value. Then, a periodic measured value is determined from the sum of the two determined first greatest half-wave measured values with the associated period interval. The period interval can be determined based on the zero transition points determined in Step 119. This period interval establishes the width of the measurement window (Step 131). The starting point $t_{m1}$ of the measurement window $t_{m1}$ is now selected such that the two first greatest (in terms of amount) half-wave measured values in succession are located within this measurement window $t_{m1}$, $t_{m2}$. With the existing signal trace according to FIG. 3a, the start of the measurement window $t_{m1}$ is set at the third zero transition point. The end of the measurement window $t_{m2}$ results from the sum of the starting point $t_{m1}$ of the measurement window and the period interval determined in Step 131 (Step 135).

The width of the interference window $t_{S1}$, $t_{S2}$ also matches the width of the measurement window $t_{m1}$, $t_{m2}$. The starting point of the interference window is selected such that the interference window $t_{S1}$, $t_{S2}$ is located within the elapsed time $t_L$ of the measurement signal $U_e$, in order to prevent the interference window $t_{S1}$, $t_{S2}$ and the measurement window $t_{m1}$, $t_{m2}$ from overlapping. The end $t_{S2}$ of the interference window is preferably located temporally ahead of the first zero transition point. The positions of the measurement and interference window $t_{m1}$, $t_{m2}$, $t_{S1}$, $t_{S2}$ are stored (Step 141). In addition, the limit values for monitoring the measurement signal $U_e$, for example, are established (Step 143). Based on the maximum value of the measurement signal $U_e$ located in the measurement window, a first limit value can be used for the monitoring of the measurement signal $U_e$ that occurs in the interference window, e.g., the first limit value is 20% of the extreme value. If the measurement signal $U_e$ in the interference window exceeds the limit value, this is an indication of an error. The program sequence for automatically establishing the measurement window is therefore ended (Step 145).

The settings of the interference window $t_{S1}$, $t_{S2}$ and the measurement window $t_{m1}$, $t_{m2}$ are retained for the subsequent welding process. In on-going operation, the ultrasonic transmitter 14 is always activated in the non-energized phase (I=0) when the trigger signal Trig appears. The measured values that are located within the measurement window $t_{m1}$, $t_{m2}$ are then evaluated to determine the attenuation or permeability D of the welded joint. To accomplish this, the energy content is determined, e.g., via the root-mean-square of the two half-waves, as described hereinabove in conjunction with Step 131. A first attenuation or permeability D0 occurs at the first trigger point T0, a second attenuation or permeability D1 occurs at the second trigger point T1, and so on. By selecting the measurement window $t_{m1}$, $t_{m2}$ in purposeful fashion and evaluating the temporal course of the measurement signal $U_e$ located only within this measurement window $t_{m1}$, $t_{m2}$, it is ensured that only suitable measurement signals $U_e$ are used in the determination of the attenuation or permeability curve D.

In the welding control unit 28, the attenuation or permeability curve D according to FIG. 4c determined in this fashion is compared with a target attenuation or permeability curve $D_{target}$ that is representative of a good weld, and the weld is constantly corrected during on-going operation via the current I. This is achieved with the controller shown in FIG. 2. The current I is therefore adjusted such that the target attenuation or permeability curve $D_{target}$ is reliably achieved.

What is claimed is:

1. A welding system, comprising:
   a device for evaluating an ultrasonic signal during a welding process, having a measured value evaluation unit (43) that, in normal operation, evaluates at least one measurement signal (Ue) that is derived from an ultrasonic signal and is located inside a measurement window ($t_{m1}$, $t_{m2}$, $t_{S1}$, $t_{S2}$), wherein at least one measurement signal (Ue) determination means (35, 37, 39) for establishing the measurement window ($t_{m1}$, $t_{m2}$, $t_{S1}$, $t_{S2}$) is provided that establish the measurement window ($t_{m1}$, $t_{m2}$, $t_{S1}$, $t_{S2}$) according to a measurement signal (Ue) that is received in a calibration operation,
   further comprising a first electrode and a second electrode, wherein material to be jointed is situated between the first electrode and second electrode, such that the material is accessible from two sides, wherein a zero transition point determination unit (37) is provided that determines the zero transition point of the amplitude of the measurement signal (Ue), whereby the measurement window ($t_{m1}$, $t_{m2}$, $t_{S1}$, $t_{S2}$) is established according to an output signal from the zero transition point determination unit (37).

2. The welding system as recited in claim 1, wherein an extreme value determination unit (39) is provided that determines at least one extreme value of the amplitude of the measurement signal (Ue), whereby the measurement window ($t_{m1}$, $t_{m2}$, $t_{S1}$, $t_{S2}$) is established according to an output signal from the extreme value determination unit (39).

3. The welding system as recited in claim 2, wherein the output signal from the extreme value determination unit (39) is compared with a limit value to generate an error signal.

4. The welding system as recited in claim 1, wherein a trigger generator (33) is provided that initiates the emission of a transmitted signal ($U_S$) that effects the measurement signal (Ue).

5. The welding system as recited in claim 1, wherein the measurement signal (Ue) is used by the device to assess a welded joint (18).

6. The welding system as recited in claim 1, wherein the device processes an ultrasonic signal, wherein said ultrasonic signal is composed of transverse waves and/or longitudinal waves.

7. The welding system as recited in claim 1, wherein the output signal from the measured value evaluation unit (43) is forwarded to a control unit (28) to generate a characteristic variable (I).

8. The welding system as recited in claim 7, wherein a trigger generator (33) initiates the emission of the transmitted signal ($U_S$) according to the characteristic variable (I).

9. The welding system as recited in claim 1, wherein an elapsed-time determination unit (35) is provided that detects the elapsed-time ($t_L$) of the measurement signal (Ue) in reaction to a transmitted signal, whereby the measurement window ($t_{m1}$, $t_{m2}$, $t_{S1}$, $t_{S2}$) is established according to an output signal ($t_L$) from the elapsed-time determination unit (35).

10. The welding system as recited in claim 9, wherein a trigger generator (33) is provided that initiates the emission of a transmitted signal ($U_S$) that effects the measurement signal (Ue).

11. The welding system as recited in claim 9, wherein the output signal from the elapsed-time determination unit (35) is compared with a limit value to generate an error signal.

12. The welding system as recited in claim 1, wherein the output signal from the zero transition point determination unit (37) is compared with a limit value to generate an error signal.

13. The welding system as recited in claim 1, wherein the output signal from the zero transition point determination unit (37) is compared with a limit value to generate an error signal.

* * * * *